United States Patent
Koyama

(10) Patent No.: US 9,041,415 B2
(45) Date of Patent: May 26, 2015

(54) WAVEGUIDE, METHOD OF MANUFACTURING THE SAME, AND ELECTROMAGNETIC WAVE ANALYSIS APPARATUS

(75) Inventor: Yasushi Koyama, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 260 days.

(21) Appl. No.: 13/599,708

(22) Filed: Aug. 30, 2012

(65) Prior Publication Data

US 2013/0063159 A1 Mar. 14, 2013

(30) Foreign Application Priority Data

Sep. 9, 2011 (JP) ................................. 2011-197123
Aug. 6, 2012 (JP) ................................. 2012-173724

(51) Int. Cl.
*G02B 6/122* (2006.01)
*B82Y 20/00* (2011.01)
*G01N 21/3581* (2014.01)

(52) U.S. Cl.
CPC ......... G02B 6/1228 (2013.01); *Y10T 29/49016* (2013.01); *G01N 21/3581* (2013.01); G02B 6/1226 (2013.01); B82Y 20/00 (2013.01)

(58) Field of Classification Search
CPC ....... G01R 27/04; G01F 23/00; G01F 23/284; G02B 6/1228; G01N 21/3581; B82V 20/00; Y10T 29/49016
USPC ........... 324/533, 639, 642, 644, 124; 73/1.73, 73/290 V
See application file for complete search history.

(56) References Cited

U.S. PATENT DOCUMENTS 7,715,667 B2 * 5/2010 Lee et al. ......................... 385/14
2007/0280319 A1 * 12/2007 Sekiguchi et al. .......... 372/45.01
2009/0134329 A1 * 5/2009 Kasai et al. ................. 250/338.1
2010/0033709 A1 2/2010 Lampin et al.

FOREIGN PATENT DOCUMENTS

JP 2010-510703 A 4/2010

OTHER PUBLICATIONS

Benjamin S. Williams et al., "Terahertz Quantum-Cascade Laser at λ ≈ 100μm Using Metal Waveguide for Mode Confinement," 83(11) Appl. Phys. Lett. 2124-2126 (Sep. 2003).
Alan Wei Min Lee et al., "High-Power and High-Temperature THz Quantum-Cascade Lasers Based on Lens-Coupled Metal-Metal Waveguides," 32(19) Optics Letters 2840-2842 (Oct. 2007).

* cited by examiner

*Primary Examiner* — Tung X Nguyen
*Assistant Examiner* — Son Le
(74) *Attorney, Agent, or Firm* — Fitzpatrick, Cella, Harper & Scinto

(57) ABSTRACT

Provided is a waveguide for guiding an electromagnetic wave between a first conductor layer and a second conductor layer each having a negative dielectric constant real part for the electromagnetic wave, the waveguide including a tapered structure in a part of the waveguide at which the electromagnetic wave exits or enters, in which a spatial profile of the tapered structure perpendicular to an optical axis extends to both sides with respect to the optical axis at least in one direction orthogonal to the optical axis as being closer to an opening plane at an outermost part of the tapered structure.

11 Claims, 6 Drawing Sheets

WAVEGUIDE, METHOD OF MANUFACTURING THE SAME, AND ELECTROMAGNETIC WAVE ANALYSIS APPARATUS

BACKGROUND OF THE INVENTION

1. Field of the Invention

The present invention relates to a waveguide, a method of manufacturing the same, and an electromagnetic wave analysis apparatus. In particular, the present invention relates to a waveguide for electromagnetic waves in frequency bands from a millimeter wave band to a terahertz wave band (30 GHz to 30 THz) (hereinafter referred to as terahertz waves), the waveguide configured to also be an oscillation device or a detection device, and methods for manufacturing the same.

2. Description of the Related Art

In the frequency band of terahertz waves, there are absorption peaks of many organic molecules in biological materials, medicines, electronic materials, and the like stemming from the structures and states thereof. Further, the terahertz waves easily penetrate materials such as paper, ceramic, resin, and cloth. In recent years, research and development have been conducted on imaging technology and sensing technology which make use of such characteristics of terahertz waves. For example, application thereof to a safe fluoroscopic apparatus to replace an X-ray apparatus, to an in-line non-destructive inspection apparatus in a manufacturing process, and the like is expected.

As a current injection type terahertz waves light source, a structure is under study, which uses an electromagnetic wave gain based on intersubband transition of electrons in a semiconductor quantum well structure. Appl. Phys. Lett. 83, 2124 (2003) proposes a terahertz waves band quantum cascade laser (QCL) in which double-side metal waveguides (hereinafter also referred to as DMWs) which are known as low loss waveguides are integrated as resonators. This device attains laser oscillation around 3 THz by light confinement at a high level and low loss propagation due to causing terahertz waves that are emitted by stimulated emission to be guided in a surface plasmon mode to a resonator structure in which metal is placed above and below a gain medium formed of a semiconductor thin film at a thickness of about 10 μm.

The DMW may cause an increase of edge reflection or beam pattern divergence due to mode mismatch between the waveguide and a space. Therefore, from viewpoint of application, there is a task of efficient use and handling of a beam. Concerning this, OPTICS LETTERS, VOL. 32, ISSUE 19, PP. 2840-2842 (2007) proposes a method of improving extraction efficiency and directivity by disposing a silicon lens at an end of the waveguide, but this method has practical problems such as being physically and mechanically unstable and requiring an additional member. Therefore, Japanese Patent Translation Publication No. 2010-510703 discloses an example in which a horn antenna is integrated. However, the structure can hardly be said to have sufficient physical and mechanical stability, and directivity of the electromagnetic wave may be tilted from an optical axis of the waveguide. Therefore, there is a room for improvement of frequency stability and handling of the electromagnetic wave.

SUMMARY OF THE INVENTION

According to an exemplary embodiment of the present invention, there is provided a waveguide for guiding an electromagnetic wave between a first conductor layer and a second conductor layer each having a negative dielectric constant real part for the electromagnetic wave, the waveguide including a tapered structure in a part of the waveguide at which the electromagnetic wave exits or enters, in which a spatial profile of the tapered structure perpendicular to an optical axis extends to both sides with respect to the optical axis at least in one direction orthogonal to the optical axis as being closer to an opening plane at an outermost part of the tapered structure.

According to the present invention, the tapered structure having the spatial profile extending as described above is disposed at the part of the waveguide at which the electromagnetic wave exits or enters. More specifically, the tapered structure having the spatial profile extending in a lamination direction of a core layer as described above is disposed at an end of a plasmon waveguide. Thus, directivity of the electromagnetic wave radiated from the waveguide or guided to the waveguide is improved. In addition, because a directivity pattern of the electromagnetic wave can be set in the optical axis direction, it is expected to improve the frequency stability and handling of the electromagnetic wave. Therefore, it is expected by the present invention to realize a waveguide and the like capable of efficiently utilizing the electromagnetic wave.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

The present invention has a feature as follows. A waveguide, which guides an electromagnetic wave between a first conductor layer and a second conductor layer each having a negative dielectric constant real part for electromagnetic waves, includes a tapered structure disposed at a part at which the electromagnetic wave enters and exits. A spatial profile of the tapered structure substantially perpendicular to an optical axis extends gradually toward both sides with respect to the optical axis at least in one direction substantially orthogonal to the optical axis as being closer to an opening plane at the outermost part of the tapered structure. More specifically, as an example described later, the waveguide is defined by the first and second conductor layers made of a negative permittivity medium having a negative dielectric constant real part for electromagnetic waves in the waveguide mode, and a core layer having a lamination structure including a semiconductor portion disposed between the two conductor layers so as to contact with the two conductor layers. Further, the tapered structure is disposed at the end of the waveguide at which the electromagnetic wave exits or enters. The spatial profile of the tapered structure extends gradually at least in the lamination direction of the core layer of the lamination structure toward both sides with respect to the lamination surface perpendicular to the lamination direction as being closer to the opening plane at the outermost part of the tapered structure. The waveguide according to the present invention can be used as a simple waveguide for electromagnetic waves, but as described later in embodiments and examples, it is possible to constitute an oscillation device, an electromagnetic wave detection device, an electromagnetic wave amplifying device, and the like by arranging the core layer to have an electromagnetic wave gain and nonlinearity.

Hereinafter, with reference to the drawings, embodiments and examples of a waveguide, a device including the same, and methods for manufacturing the waveguide and the device according to the present invention are described.

Embodiment

Figure 1:
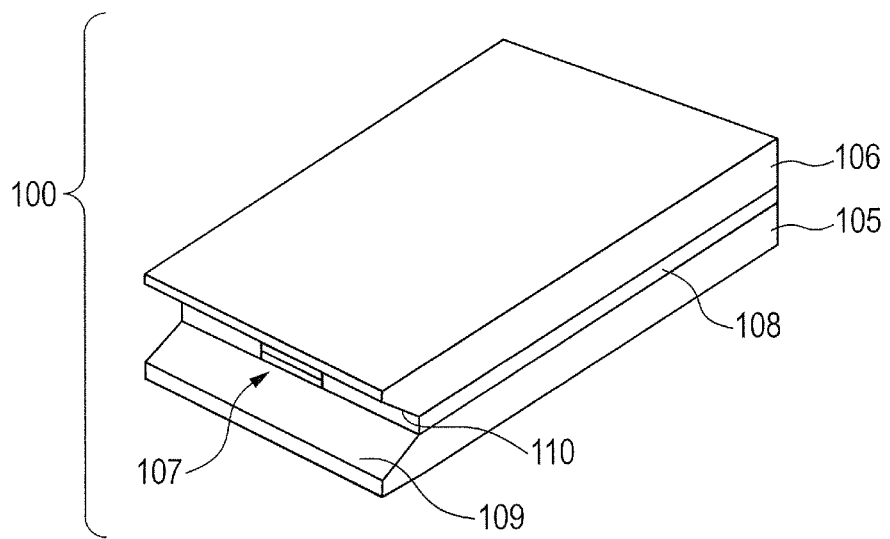
FIG. 1 is a perspective view illustrating a waveguide according to an embodiment and Example 1 of the present invention.
Figure 2A:
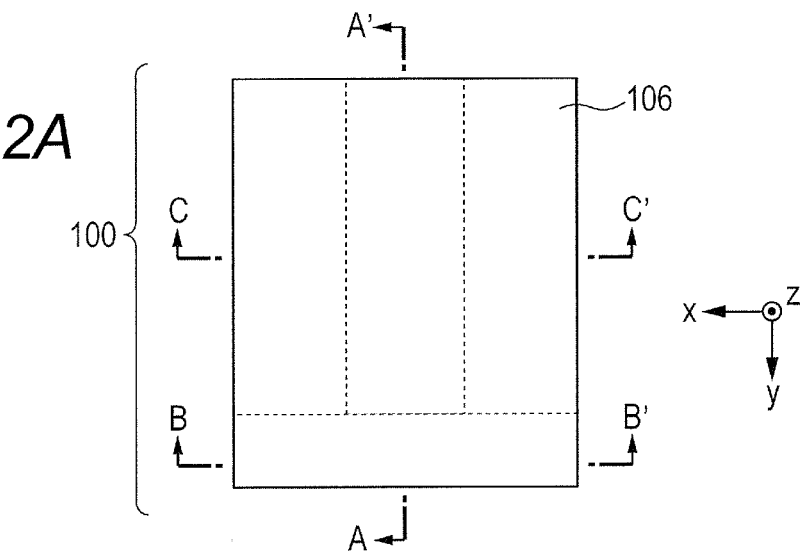
FIG. 2A is a diagram illustrating the waveguide according to the embodiment and Example 1 of the present invention.
Figure 2B:
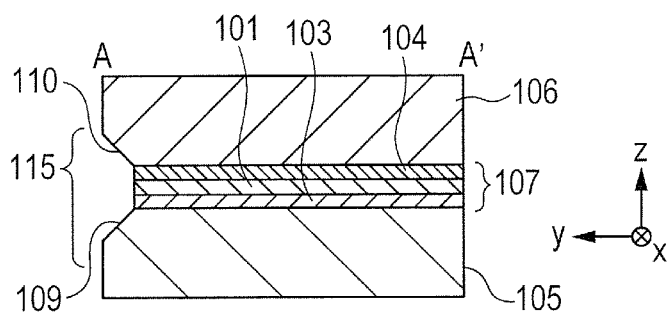
FIG. 2B is a diagram illustrating the waveguide according to the embodiment and Example 1 of the present invention.
Figure 2C:
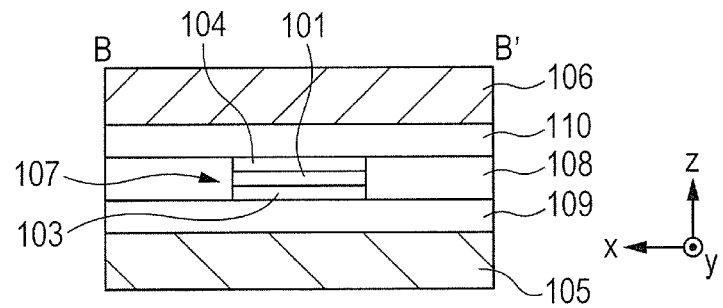
FIG. 2C is a diagram illustrating the waveguide according to the embodiment and Example 1 of the present invention.
Figure 2D:
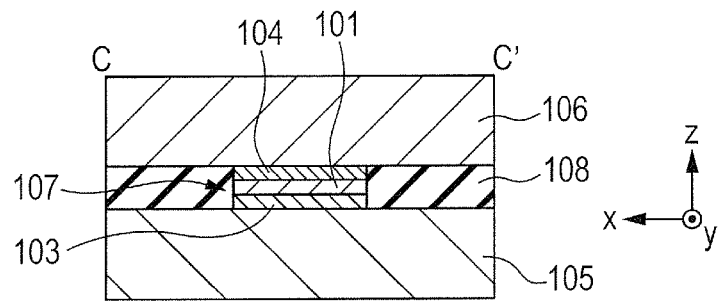
FIG. 2D is a diagram illustrating the waveguide according to the embodiment and Example 1 of the present invention.
Figure 3A:
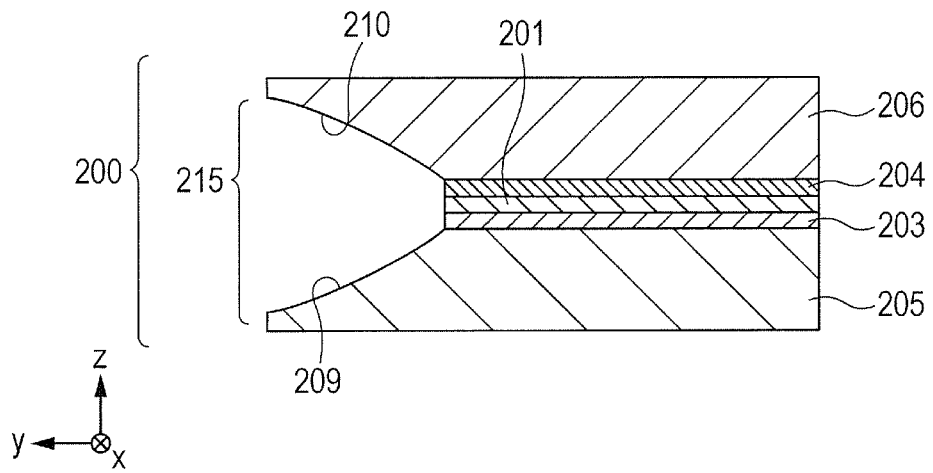
FIG. 3A is a diagram illustrating a waveguide according to a modified example of the present invention.
Figure 3B:
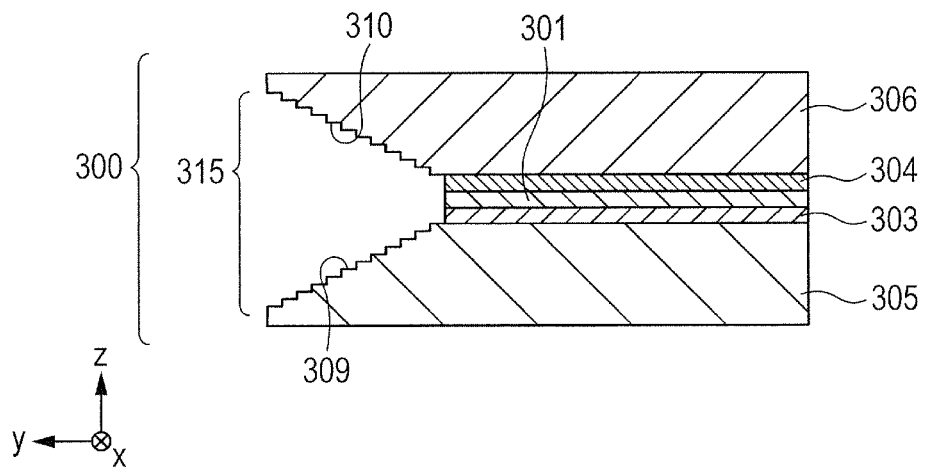
FIG. 3B is a diagram illustrating the waveguide according to a modified example of the present invention.
Figure 3C:
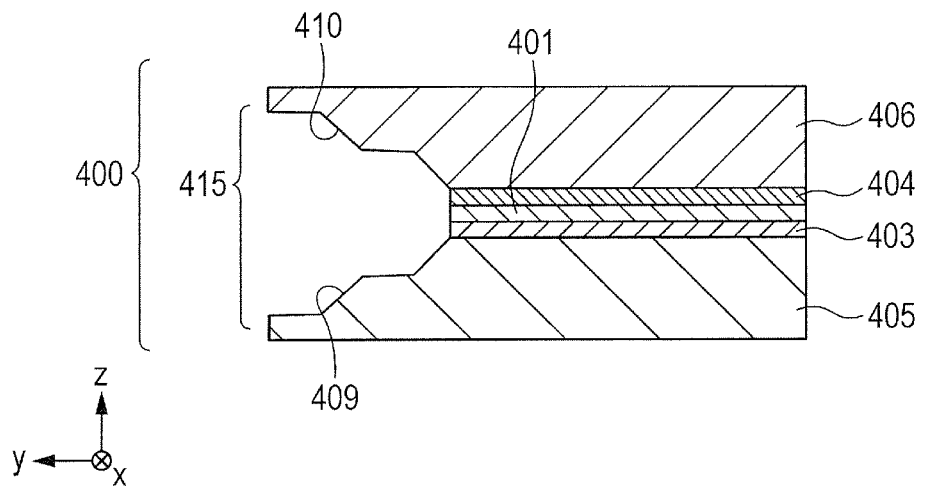
FIG. 3C is a diagram illustrating the waveguide according to a modified example of the present invention.

A waveguide 100 according to an embodiment of the present invention is described with reference to FIGS. 1 to 3C. FIG. 1 is a schematic diagram illustrating an external appearance of the waveguide 100. FIGS. 2A, 2B, 2C, and 2D are schematic diagrams illustrating a top view, an A-A' cross-sectional view, a B-B' cross-sectional view, and a C-C' cross-sectional view of the waveguide 100, respectively. FIGS. 3A to 3C are schematic cross-sectional views of a modified example of this embodiment.

The waveguide 100 of this embodiment is an oscillation device including a waveguide structure 107 as a resonator, which is formed of and defined by an active layer 101 that is a core layer having an electromagnetic wave gain, a first conductor layer 103, and a second conductor layer 104. The waveguide structure 107 is integrated on a first substrate 105, a second substrate 106 is disposed on the waveguide structure 107, and spacers 108 are disposed on the sides of the waveguide structure 107. The waveguide structure 107 is an optical waveguide called a DMW in which the first conductor layer 103 and the second conductor layer 104 as a clad, which are two conductive plates close to each other, sandwich the active layer 101 as a core. The first conductor layer 103 and the second conductor layer 104 are made of a negative permittivity medium having a negative dielectric constant real part for electromagnetic waves in an oscillation mode. The distance between the first conductor layer 103 and the second conductor layer 104 is equal to or smaller than $\lambda_g/2$, preferably about $\lambda_g/10$, where $\lambda_g$ is the guide wavelength of the waveguide 100 in an oscillation mode. At this time, an electromagnetic wave in a frequency band of terahertz waves propagates through the waveguide structure 107 in a plasmon mode in which no diffraction limit exists. The guide wavelength ($\lambda_g$) is expressed by $\lambda_g = \lambda/n_e$, where $\lambda$ is the wavelength of the electromagnetic wave in a vacuum and $n_e$ is the equivalent refractive index of the waveguide structure 107. Further, in order to obtain the oscillation mode in which the guide wavelength is $\lambda_g$, as is known in the field of the semiconductor laser technology, a length L of the waveguide structure 107 in a longitudinal direction which is a propagation direction of the electromagnetic wave is set to be an integral multiple of $\lambda_g/2$.

The active layer 101 includes a semiconductor portion having a multiple quantum well structure for generating terahertz waves by intersubband transition of carriers, and has an electromagnetic wave gain in the frequency band of terahertz waves. As the active layer 101, for example, a resonant tunnel structure including a semiconductor multilayer of several tens of layers or a quantum cascade laser structure including a semiconductor multilayer of several hundreds to several thousands of layers is suitable. This embodiment is described as a case in which a resonant tunnel diode (hereinafter also referred to as RTD) is used as the active layer 101. An RTD has an electromagnetic wave gain in the frequency band of millimeter waves to terahertz waves based on the photon-assisted tunneling phenomenon in the negative differential resistance region. Note that, the active layer 101 may have a semiconductor layer doped at a high concentration so as to connect the semiconductor portion in the multiple quantum well structure with the first conductor layer 103 and the second conductor layer 104. The active layer 101 having the lamination structure defines the lamination direction and the lamination surface perpendicular to the lamination direction. In addition, the active layer 101 may be a semiconductor having carrier nonlinearity in the frequency band of terahertz waves. In this case, the waveguide 100 works as a detection device.

The active layer 101 is in contact with the first conductor layer 103 and the second conductor layer 104 mechanically and electrically, respectively. The waveguide 100 has a structure in which a bias is applied between the first conductor layer 103 and the second conductor layer 104 from an external power supply so as to apply a bias to the RTD of the active layer 101. In this case, as the first conductor layer 103 and the second conductor layer 104, a metal (Ag, Au, Cu, Al, a AuIn alloy, or the like), a semimetal (Bi, Sb, ITO, ErAs, or the like), or a semiconductor doped at a high concentration may be suitably used. In addition, as power supply lines from the first conductor layer 103 and the second conductor layer 104 to the external power supply, it is preferred to use through wirings (not shown) such as through holes formed in the first substrate 105 and the second substrate 106.

The waveguide 100 of this embodiment includes a tapered structure 115 having a spatial profile gradually extending toward both sides with respect to the lamination surface at least in the lamination direction of the active layer 101 at an end of the waveguide structure 107 from which the electromagnetic wave exits. The tapered structure 115 has a structure including at least a first surface 109 formed on the first substrate 105 and a second surface 110 formed on the second substrate 106, as illustrated in FIGS. 2B and 2C. The first surface 109 and the second surface 110 form an acute angle (75 degrees in this embodiment) with respect to the lamination direction of the active layer 101 (z axis) and are opposed to each other. In other words, the first surface 109 and the second surface 110 inclined to the lamination direction of the core layer are disposed so as to be opposed to each other at an acute angle (15 degrees in this embodiment) with respect to an optical axis of the waveguide structure 107 (y axis). Therefore, the waveguide 100 has a structure including a horn antenna 115 with an E-plane (surface of FIG. 2B) fan-shaped horn as the tapered structure 115 at an end of the waveguide structure 107 (the tapered structure 115 is hereinafter described as the horn antenna 115). In this way, the waveguide 100 of this embodiment has a structure in which the horn antenna extending toward both sides in the direction between electrodes, as a horn antenna gradually extending an opening of a waveguide tube for matching to free space, is disposed at an output portion of the waveguide and is formed integrally to the substrates 105 and 106. This output portion of the plasmon waveguide may be a receiving portion of the electromagnetic wave when the above-mentioned structure is used as a detection device, an amplifying device, or a simple waveguide.

Here, it is preferred that inner walls of the horn antenna 115, particularly the first surface 109 and the second surface 110, be made of a conductive material such as a metal, a semimetal, or a semiconductor doped at a high concentration. For instance, the waveguide 100 uses a structure in which parts of the substrates 105 and 106 are coated with Au having high conductivity as the first surface 109 and the second surface 110. A conductive material such as a metal, a semimetal, or a semiconductor doped at a high concentration may be used for the substrates 105 and 106 themselves. In addition, it is preferred that the waveguide 100 have a structure such that a high frequency electromagnetic field propagating in the waveguide structure 107 is coupled to the horn antenna 115. For instance, in the case of this embodiment, the first surface 109 and the first conductor layer 103, as well as the second surface 110 and the second conductor layer 104 are respectively connected to each other electrically and mechanically. Therefore, the Au-coated inclined surfaces 109 and 110 of the horn antenna 115 are extended from the conductor layers 103 and 104 that are parallel flat electrodes of the plasmon waveguide. In this way, the structure of this embodiment includes the first substrate 105 that is in contact with the first conductor layer and has the first surface, and the second substrate 106 that is in contact with the second conductor layer and has the second surface. In this structure, the first substrate, the first conductor layer, the core layer, the second conductor layer, and the second substrate are laminated in this order.

In addition, it is preferred that the waveguide 100 have a structure in which a bias can be stably applied to the active layer 101 having the electromagnetic wave gain in the waveguide structure 107. For instance, in this embodiment, the spacer 108 maintains mechanical stability of the waveguide structure 107 and prevents a short circuit between the electrodes 103 and 104 as a DC-cut device. In addition, the Au-coated inclined surfaces 109 and 110 of the horn antenna 115 are DC-cut by the space so that a short circuit between the electrodes 103 and 104 is prevented. Therefore, the waveguide 100 has a structure in which both the stable bias application to the RTD and coupling between the horn antenna 115 and the waveguide structure 107 are achieved.

Figure 6:
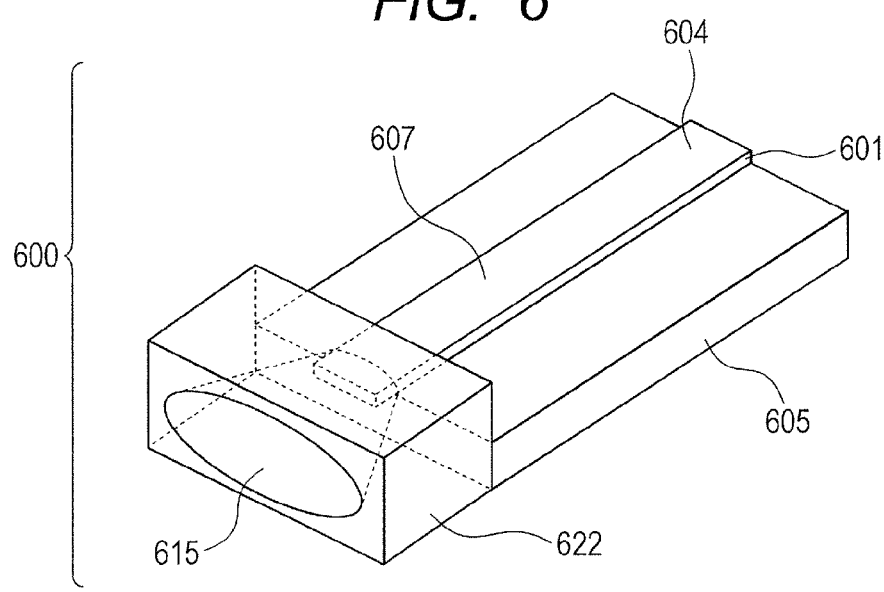
FIG. 6 is a perspective view illustrating a waveguide according to a modified example of the present invention.

Note that, the spacer 108 is not necessarily an essential device, and there may be adopted a structure in which the horn antenna 115 has a DC-cut portion. In addition, the coupling between the waveguide structure and the antenna does not necessarily have the above-mentioned structure like a DC coupling. For instance, there may be adopted a structure as in a waveguide 600 illustrated in FIG. 6, in which a waveguide structure 607 and an antenna 615 are AC coupled. The waveguide 600 has a structure in which an end face of the microstrip-line type waveguide structure 607 on one side is inserted in the inner space of the horn antenna 615 having a tapered structure (or is drawn out from the inner space) through a bottom opening having a smallest cross sectional area. By adjusting the position, impedance matching between the waveguide structure 607 and the horn antenna 615 can be performed. In this case, a member constituting the antenna may not be necessarily connected mechanically to the two conductor layers 604 and 605 constituting the waveguide structure including a core layer 601.

The waveguide of this embodiment includes, at the end of the plasmon waveguide, the horn antenna having a spatial profile extending gradually to both sides with respect to the lamination surface of the active layer in the lamination direction of the active layer as being closer to the opening plane at the outermost part. In other words, this horn antenna has the first surface 109 and the second surface 110 that are opposed inclined surfaces. This structure enables improvement of directivity of the electromagnetic wave radiated from the end face of the waveguide with a wide radiation angle. In addition, by forming a symmetric structure of the horn with respect to the lamination surface of the active layer, it is expected to further reduce the tilt of the directivity pattern of the electromagnetic wave with respect to the optical axis direction of the waveguide. Therefore, it is possible to stabilize the directivity pattern of the electromagnetic wave in the optical axis direction so that handling of the electromagnetic wave becomes easy. In addition, it is expected to reduce instability of the tilt of the electromagnetic wave and frequency characteristics caused by the form of the antenna structure or physical or mechanical instability. Further, the waveguide of this embodiment has a structure in which the plasmon waveguide and the horn antenna can be integrally formed by a fine processing technology such as micromachining. In other words, the waveguide of this embodiment can be applied to a three-dimensional structure in which two or more substrates are integrated. Therefore, it is expected to improve physical and mechanical stability and accuracy of processing. In addition, it is also expected to reduce the cost by reducing the number of optical components such as lenses. Thus, according to this embodiment, it is possible to realize a small and durable waveguide capable of efficiently utilizing the electromagnetic wave, and a semiconductor device such as an oscillation device or a detection device using the waveguide.

The present invention is not necessarily limited to the above-mentioned structure. For instance, as the modified example of this embodiment illustrated in FIGS. 3A to 3C, a shape and symmetry of the tapered structure can be designed appropriately in accordance with a desired directivity pattern or frequency characteristics. A waveguide 200 illustrated in FIG. 3A includes a horn antenna 215 in which tapered surfaces 209 and 210 are formed of curved surfaces. Here, each member is denoted by numeral of 200s. In addition, a waveguide 300 in FIG. 3B may include a horn antenna 315 having a multi-step flare structure in which tapered surfaces 309 and 310 form multiple steps. Here, supposing the step-like structure has a size of approximately 1/10 of the wavelength of the electromagnetic wave, influences of reflection, scattering, and refraction on the electromagnetic wave of the wavelength can be generally neglected. Therefore, the step-like structure can be regarded as a substantially inclined surface. Here, each member is denoted by numeral of 300s. In addition, as illustrated in FIG. 3C, a waveguide 400 may include a horn antenna 415 in which tapered surfaces 409 and 410 have a step structure. Here, each member is denoted by numeral of 400s. In each modified example, it should be understood that the tapered structure does not necessarily have a symmetric structure with respect to the lamination surface of the active layer, and an appropriate structure may be selected in accordance with a desired beam shape and directivity. In addition, it is expected to improve radiation pattern and directivity of the antenna by forming the tapered structure to have an exponential type or Fermi distribution function type tapered shape.

Figure 4:
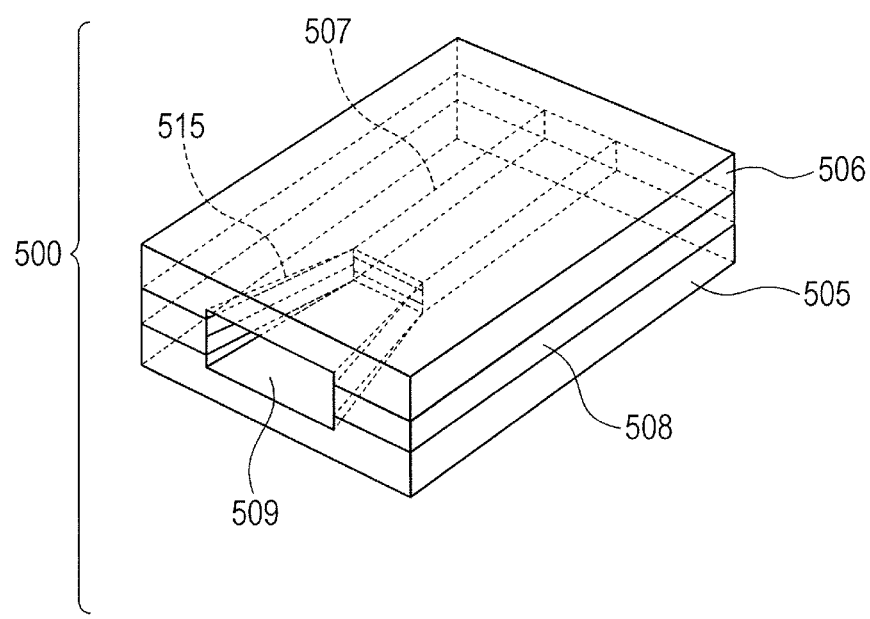
FIG. 4 is a perspective view illustrating a waveguide according to Example 2 of the present invention.
Figure 5A:
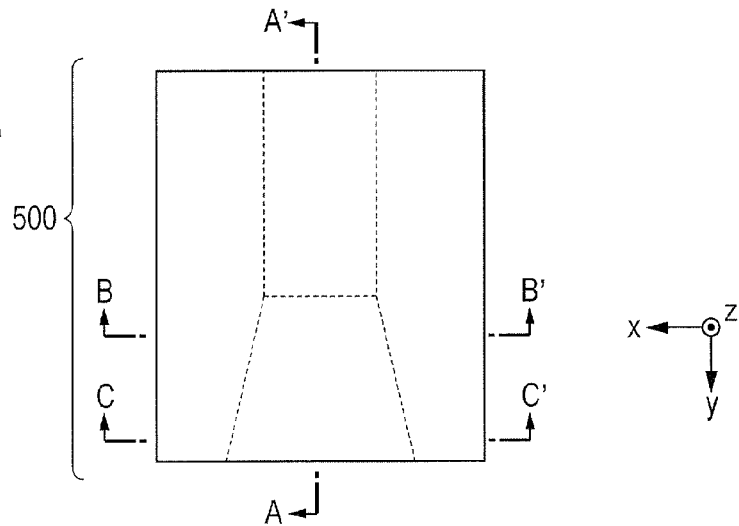
FIG. 5A is a diagram illustrating the waveguide according to Example 2 of the present invention.
Figure 5B:
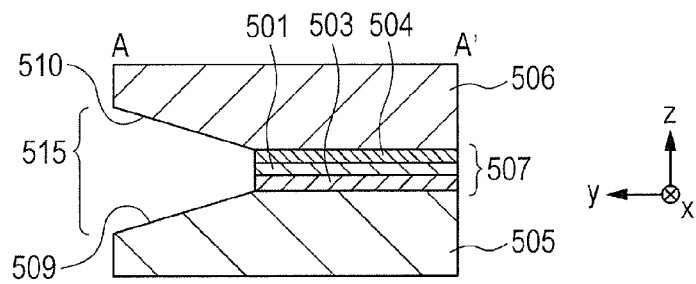
FIG. 5B is a diagram illustrating the waveguide according to Example 2 of the present invention.
Figure 5C:
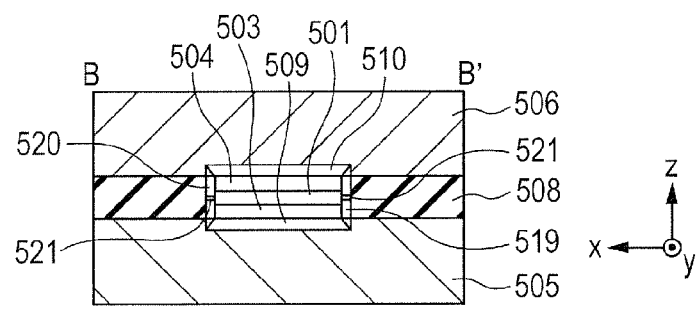
FIG. 5C is a diagram illustrating the waveguide according to Example 2 of the present invention.
Figure 5D:
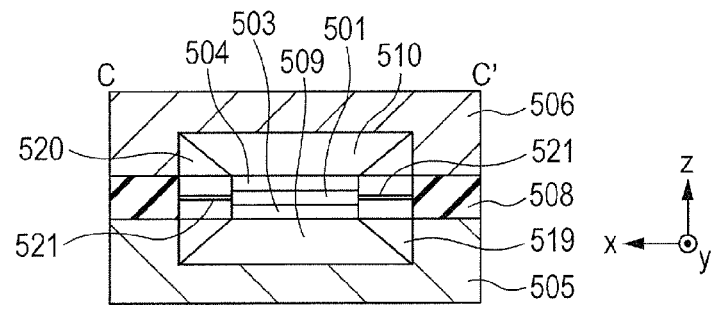
FIG. 5D is a diagram illustrating the waveguide according to Example 2 of the present invention.

In addition, the direction in which the spatial profile of the tapered structure is extended is not limited to the lamination direction of the active layer. A waveguide 500 as another modified example of this embodiment is illustrated in FIGS. 4 and 5A to 5D. FIG. 4 is a schematic diagram illustrating an external appearance of the waveguide 500. FIGS. 5A, 5B, 5C, and 5D are schematic diagrams illustrating a top view, an A-A' cross-sectional view, a B-B' cross-sectional view, and a C-C' cross-sectional view of the waveguide 500, respectively. This waveguide 500 includes a pyramidal horn antenna 515. Here, tapered surfaces 509 and 510, and tapered surfaces 519 and 520 define the spatial profile that is perpendicular to the optical axis and extends to both sides in the lamination direction of an active layer 501 and to both sides in the direction perpendicular to the lamination direction (direction orthogonal to the lamination direction and the optical axis). It is preferred to use this structure for adjusting directivity pattern in a lateral direction (direction orthogonal to the lamination direction of the active layer and the optical axis) of a waveguide structure 507 for the electromagnetic wave radiated from the waveguide structure 507 of the waveguide 500. In addition, the structure of the waveguide 600 illustrated in FIG. 6 having a conical horn with a curved surface extending radially as the horn antenna 615 is suitable for coupling an electromagnetic wave radiated from the waveguide structure 607 to a circular waveguide tube.

In addition, in the waveguide of the present invention, the waveguide structure and the antenna may not be necessarily integrated on the same substrate. For instance, as in the waveguide 600 as the modified example of this embodiment, the waveguide may have a structure in which a substrate 622 on which the horn antenna 615 is formed is mounted on the substrate 605 on which the waveguide structure 607 is integrated. By using another substrate 622, flexibility of design and processing of the antenna is improved. As a result, even the structure having a free curved surface like the conical horn adopted in the horn antenna 615 can be used relatively easily. Note that, the waveguide 600 has a structure in which the waveguide structure 607 and the antenna 615 are AC-coupled as described above. In other words, in this case too, the tapered structure is electrically coupled to the waveguide structure.

In addition, in the waveguide of the present invention, a type of the waveguide is not limited to the DMW. For instance, the tapered structure of the present invention may be disposed in the microstrip-line type waveguide 600 illustrated in FIG. 6 or a waveguide including a structure such as a coplanar transmission line, a hollow waveguide tube, a patch antenna resonator, a slot antenna resonator, or the like.

In addition, the waveguide of the present invention and the semiconductor device such as the oscillation device or the detection device using the waveguide can be manufactured by the following steps. For instance, a method of manufacturing the waveguide formed of the clad made of the first conductor layer and the second conductor layer disposed close to each other with a distance of a guide wavelength ($\lambda_g$) or smaller, and the core layer made of the semiconductor layer disposed between the two conductor layers, includes at least the following steps (A) to (D). In addition, when the semiconductor layer includes the active layer having an electromagnetic wave gain and nonlinearity, the oscillation device or the detection device including the waveguide as the resonator is manufactured.

(A) a step of forming on the first substrate a first surface inclined in the thickness direction of the first substrate (B) a step of forming on the second substrate a second surface inclined in the thickness direction of the second substrate (C) a step of bonding the first conductor layer to the first substrate (D) a step of bonding the second conductor layer to the second substrate so that the first surface and the second surface are opposed to each other in the thickness direction of the core layer.

Hereinafter, more specific examples are described.

Example 1

Specific Example 1 of the waveguide according to the present invention is described with reference to FIGS. 1 and 2A to 2D. Here, the waveguide according to the present invention can be used as a simple waveguide for electromagnetic waves, but it is possible to constitute the semiconductor device such as an oscillation device, an electromagnetic wave detection device, and an electromagnetic wave amplifying device by arranging the core layer to have an electromagnetic wave gain and nonlinearity. Therefore, in the following description, as an example thereof, there is described an example in which the waveguide of the present invention is used for the oscillation device. In this example, as the semiconductor multiple quantum well structure for generating terahertz waves by intersubband transition, an InGaAs/InAlAs-based resonant tunnel diode (RTD) structure which was lattice matched to an InP substrate was used. The RTD structure has a semiconductor multilayer structure in which n-InGaAs (50 nm, Si, $1\times10^{18}$ cm$^{-3}$), InGaAs (5 nm), AlAs (1.3 nm), InGaAs (7.6 nm), InAlAs (2.6 nm), InGaAs (5.6 nm), AlAs (1.3 nm), InGaAs (5 nm), and n-InGaAs (50 nm, Si, $1\times10^{18}$ cm$^{-3}$) are stacked in the stated order from the top. The underlined InGaAs layers are to be quantum well layers, while InAlAs-based materials which are not underlined are to be potential barrier layers to form a triple barrier resonant tunnel structure. The AlAs which are not lattice matched to the InP are thinner than a critical thin film and are high energy barriers. Further, the n-InGaAs layers at the top and at the bottom which are doped with high density carriers are emitter/collector layers for injecting/extracting electrons into/from the resonant tunnel structure. The InGaAs (5 nm) placed between the emitter/collector layers and the potential barrier layers, respectively, are layers for preventing diffusion of Si as a doping material.

The active layer 101 includes the RTD structure and the n-InGaAs ($1\times10^{19}$ cm$^{-3}$) which are placed above and below the RTD structure and which are doped with the high density carriers. The thickness of the active layer 101 is about 1 μm. The doping layers connect the RTD structure and the second conductor layer 104 and the first conductor layer 103, respectively, with relatively low resistance. Each of the first conductor layer 103 and the second conductor layer 104 is a film formed by stacking Ti/Pd/Au. The first conductor layer 103 is Ti/Pd/Au/Pd/Ti (having thicknesses of 20 nm/20 nm/400 nm/20 nm/20 nm, respectively) and the second conductor layer 104 is Ti/Pd/Au/Pd/Ti (having thicknesses of 20 nm/20 nm/400 nm/20 nm/20 nm, respectively). The substrate 105 is a high resistance silicon substrate, and is mechanically connected to the first conductor layer 103. In addition, the substrate 106 is a high resistance silicon substrate, and is mechanically connected to the second conductor layer 104. In addition, the substrate 105 and the substrate 106 are mechanically connected via the spacer 108 in the region without the waveguide structure 107. It is preferred that the spacer 108 be made of an insulation material with low loss in the terahertz band (for example, a resin such as BCB, or an inorganic material such as $SiO_2$), and benzocyclobutene (BCB) is used in this example. The oscillation device 100 is connected to a power supply via through wirings (not shown) connected to the second conductor layer 104 and the first conductor layer 103 so that a bias voltage for driving is supplied to the active layer 101.

In the waveguide 100, the substrate 105 includes the first surface 109, and the substrate 106 includes the second surface 110. The waveguide structure 107 and the horn antenna 115 are integrally formed. The first surface 109 is a surface inclined by 15 degrees with respect to the y axis, and a surface thereof is coated with conductive materials of Ti/Pd/Au (having thicknesses of 20 nm/20 nm/200 nm, respectively). In addition, the second surface 110 is a surface inclined by 15 degrees with respect to the y axis, and a surface thereof is coated with conductive materials of Ti/Pd/Au (having thicknesses of 20 nm/20 nm/200 nm, respectively). The first surface 109 and the first conductor layer 103, as well as the second surface 110 and the second conductor layer 104 are electrically and mechanically connected to each other. The horn antenna 115 is a fan-shaped horn in which an opening width in the z axis direction is 5 mm, an opening width in the x axis direction is 10 mm, an opening angle in the z axis direction is 30 degrees, and a length between the opening plane at the outermost part and the end face of the waveguide structure 107 is 9.3 mm.

The waveguide structure 107 has a Fabry-Perot resonator structure, and includes at least two end faces in the propagation direction of the electromagnetic wave. The electromagnetic wave is caused to be standing wave by using reflection from the end faces, and hence the length in the propagation direction of the waveguide structure 107 (longitudinal direction of the waveguide structure 107) is a factor in determining the oscillation wavelength. In this example, the length of the waveguide structure 107 is 1 mm, which is 20 times as large as $\lambda_g$, and the width of the waveguide structure 107 is 0.05 mm. Therefore, the first conductor layer 103 and the second conductor layer 104 are each in a rectangular pattern of 1 mm×0.05 mm. In addition, the first conductor layer 103 and the second conductor layer 104 are close to each other with a distance of approximately 1 μm. The waveguide structure 107 is designed such that the oscillation frequency is 0.3 THz, and the guide wavelength $\lambda_g$ is 50 μm (an equivalent refractive index of the waveguide structure is set to be approximately 20). The electromagnetic wave propagates in the waveguide structure 107 in a plasmon mode, in which the end face of the waveguide structure 107 becomes an open end, and a position at $\lambda_g/4$ from the end face becomes a node of the resonance electric field. The waveguide 100 radiates an electromagnetic wave of 0.3 THz generated based on a photon-assisted tunneling effect in a negative differential resistance region from the horn antenna 115 disposed at the end of the waveguide structure 107.

The waveguide 100 of this example can be manufactured by the following manufacturing method.

(1) Prepare the first substrate 105 made of silicon, and form the first surface 109 having an acute angle with the thickness direction by a photolithography method and a Si Deep RIE process. Form metal layers of Ti/Pd/Au (having thicknesses of 20 nm/20 nm/200 nm, respectively) on an upper surface of the first substrate 105 and a surface of the first surface 109. This step corresponds to the above-mentioned step (A).

(2) Prepare the second substrate 106 made of silicon, and form the second surface 110 having an acute angle with the thickness direction by the photolithography method and the Si Deep RIE process. Form metal layers of Ti/Pd/Au (having thicknesses of 20 nm/20 nm/200 nm, respectively) on an upper surface of the second substrate 106 and the surface of the second surface 110. Shape the metal layers by the photolithography method and a dry etching method. Fill the pattern of the metal layer with BCB by a spin coat method and the dry etching method, and smooth the pattern so as to form the pattern of the metal layer and the BCB on the upper surface of the second substrate 106. This step corresponds to the above-mentioned step (B).

(3) Prepare an InP substrate on which a semiconductor layer including the active layer 101 is epitaxially grown. Form metal layers of Ti/Pd/Au (having thicknesses of 20 nm/20 nm/200 nm, respectively) on an upper surface of the semiconductor layer. Arrange the InP substrate and the upper surface of the first substrate 105 to be opposed to each other and bond the two substrates by an Au thermocompression bonding method. Here, the Ti/Pd/Au/Pd/Ti (having thicknesses of 20 nm/20 nm/400 nm/20 nm/20 nm, respectively) formed by the compression bonding become the first conductor layer 103. This step corresponds to the above-mentioned step (C). Therefore, the first conductor layer 103 and the first surface 109 are formed of the integrated metal films. Remove the InP substrate from the bonded and integrated substrate by grinding and hydrochloric acid etching so as to transfer the semiconductor layer onto the first substrate 105. Shape the semiconductor layer and the first conductor layer 103 by the photolithography method and the dry etching method. Using a vacuum deposition method and a lift-off method, form the second conductor layer 104 made of Ti/Pd/Au (having thicknesses of 20 nm/20 nm/200 nm, respectively) on the semiconductor layer so as to shape the structure of the waveguide structure 107. Fill the structure of the waveguide structure 107 with BCB by the spin coat method and smooth the structure by the dry etching method.

(4) Arrange the upper surface of the second substrate 106 and the upper surface of the first substrate 105 to be opposed to each other so as to bond the two substrates by thermocompression bonding of an Au—Au pattern and a BCB-BCB pattern. In this case, alignment is performed so that the first surface 109 and the second surface 110 are opposed to each other in the thickness direction of the semiconductor layer. In this case, the metal layer of the second substrate 106 and the second conductor layer 104 are connected to each other so that the second conductor layer 104 and the second surface 110 are formed as an integrated metal film. This step corresponds to the above-mentioned step (D).

The present invention is not limited to the above-mentioned structure of this example. For example, in this example, the active layer 101 described above is a triple barrier resonant tunnel diode formed of InGaAs/InAlAs and InGaAs/AlAs grown on an InP substrate. However, the present invention is not limited to the structure and the materials, and other structures and other combinations of materials may also provide a waveguide according to the present invention such as an oscillation device. For example, a resonant tunnel diode having a double barrier quantum well structure, a resonant tunnel diode having a multiple barrier quantum well structure of quadruple or more, a multiple quantum well structure having cascade connections as is known by a quantum cascade laser, a rectifying device such as a Schottky barrier diode or a negative resistance device such as a Gunn diode may also be used. Any of those is suitable for an oscillation device, a detection device, and an amplifying device. With regard to the combination of materials, GaAs/AlGaAs, GaAs/AlAs, or InGaAs/GaAs/AlAs formed on a GaAs substrate, InGaAs/AlGaAsSb formed on an InP substrate, InAs/AlAsSb or InAs/AlSb formed on an InAs substrate, Si/SiGe formed on a Si substrate, or the like may also be used. The structure and the materials may be appropriately selected depending on the desired frequency and the like. Further, the material of the substrate may be selected depending on the application purpose, and a semiconductor substrate such as a silicon substrate, a gallium arsenide substrate, an indium arsenide substrate, or a gallium phosphorus substrate, a glass substrate, a ceramic substrate, a resin substrate, or the like may also be used.

Further, as the spacer, an inorganic material such as $SiO_2$, polysilicon, $SiN_x$, AlN, or $TiO_2$ or an organic material such as BCB (benzocyclobutene), SU-8, or a polyimide is suitably used. Further, a low conductive intrinsic semiconductor which is regrown may also be used. In addition, the method of manufacturing the device according to the present invention is not limited to the above-mentioned method. For instance, micromachining using a femtosecond laser or an ultrasonic wave, or conventional NC machining may be used.

Example 2

A waveguide 500 according to Example 2 of the present invention is now described with reference to FIGS. 4 and 5A to 5D. An active layer 501 uses the quantum cascade laser structure disclosed in Appl. Phys. Lett. 83, 2124 (2003). The active layer 501 is a semiconductor multilayer at a thickness of about 10 μm. With regard to a first conductor layer 503 and a second conductor layer 504, the DMW structure is used. Further, with regard to other constituent materials such as a substrate 505, a substrate 506, and a spacer 508, the same configurations as in Example 1 are used, and those components are manufactured by substantially the same manufacturing method. In a waveguide structure 507, the conductor layers 503 and 504 are in a rectangular pattern of about 2.6 mm×0.15 mm, and are designed to obtain oscillation of about 3 THz. In this structure, the equivalent refractive index of the waveguide structure 507 when the oscillation frequency is 3 THz is about 3, and the guide wavelength $\lambda_g$ is about 30 μm.

The waveguide 500 of this example has a structure in which the pyramidal horn antenna 515 is integrally formed on the end of the waveguide structure 507. The horn antenna 515 has the tapered structure including the surfaces 509 and 510 extending to both sides in the lamination direction of the active layer 501, and the surfaces 519 and 520 extending to both sides in the direction perpendicular to the lamination direction. The surfaces 509 and 510 are surfaces inclined by 10 degrees with respect to the y axis, and the surfaces thereof are coated with the conductive materials Ti/Pd/Au (having thicknesses of 20 nm/20 nm/200 nm, respectively). In addition, the surfaces 519 and 520 are surfaces inclined by 10 degrees with respect to the y axis, and the surfaces thereof are partially coated with the conductive materials Ti/Pd/Au (having thicknesses of 20 nm/20 nm/200 nm, respectively). The surface 509 and parts of the surfaces 519 and 520 are electrically connected to a first conductor layer 503. The surface 510 and parts of the surfaces 519 and 520 are electrically connected to a second conductor layer 504. In the surfaces 519 and 520, the region that is not coated with the conductive member is a DC-cut portion 521. The horn antenna 515 has a pyramidal horn shape in which the opening width in the z axis direction is 0.5 mm, the opening width in the x axis direction is 1 mm, the opening angle in the z axis direction is approximately 20 degrees, the opening angle in the x axis direction is approximately 40 degrees, and the length between the opening plane at the outermost part and the end of the waveguide structure 507 is 1.4 mm.

It is preferred to use this structure when adjusting the directivity pattern of the electromagnetic wave radiated from the waveguide structure 507 of the waveguide 500 in a lateral direction of the waveguide structure 507 (direction perpendicular to the lamination direction of the active layer).

Example 3

An electromagnetic wave analysis apparatus as Example 3 of the present invention is described with reference to FIG. 7.

Figure 7:
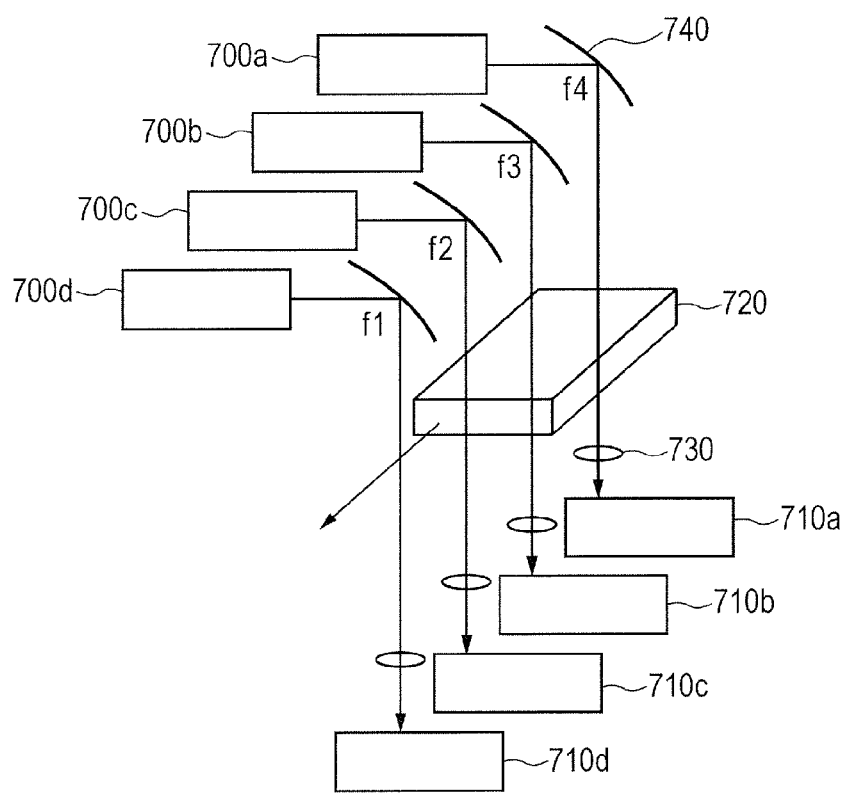
FIG. 7 is a diagram illustrating an electromagnetic wave analysis apparatus of the present invention.

As illustrated in FIG. 7, the electromagnetic wave analysis apparatus of this example has a structure in which oscillation devices 700a to 700d for oscillating electromagnetic waves including the waveguide described in Example 1, for example, are arranged and aligned, and electromagnetic waves of oscillation frequencies f1 to f4 are generated. In addition, each of the electromagnetic waves propagates as a collimated beam via a parabolic mirror 740 and irradiates an object 720 to be inspected. The transmitted light is condensed by a lens 730 and is received by one of detection devices 710a to 710d. Here, the detection devices 710a to 710d are detection devices for detecting the electromagnetic wave including the waveguide described above in Example 1. Note that, the transmitted light inspection is adopted in this example, but a reflection light inspection may be adopted.

For instance, a combination pattern of intensity of the electromagnetic wave to be received by the detection devices 710a to 710d is stored in a storage device in advance. In addition, it is supposed that the object 720 to be inspected has at least one specific absorption spectrum among the frequencies f1 to f4. In this case, by comparing the absorption spectrum of the object 720 to be inspected with the stored pattern, it is possible to determine whether or not a material to be inspected is contained in the object 720. Note that, the waveguide of the present invention is used for the oscillation device and the detection device in this example, but it is possible to realize the electromagnetic wave analysis apparatus capable of efficiently utilizing the electromagnetic wave by using the waveguide of the present invention for at least one of the oscillation device and the detection device.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-197123, filed Sep. 9, 2011, and Japanese Patent Application No. 2012-173724, filed Aug. 6, 2012, which are hereby incorporated by reference herein in their entirety.

What is claimed is:

1. A waveguide for guiding an electromagnetic wave between a first conductor layer and a second conductor layer each having a negative dielectric constant real part for the electromagnetic wave, the waveguide comprising a tapered structure in a part of the waveguide at which the electromagnetic wave exits or enters,
   wherein a spatial profile of the tapered structure perpendicular to an optical axis extends to both sides with respect to the optical axis at least in one direction orthogonal to the optical axis as being closer to an opening plane at an outermost part of the tapered structure, and wherein the first conductor layer and the second conductor layer are close to each other by a distance of a guide wavelength $\lambda_g = \lambda/n_e$ or smaller in one of a waveguide mode and an oscillation mode, where $\lambda$ represents a wavelength of the electromagnetic wave, and $n_e$ represents an equivalent refractive index of the waveguide.

2. The waveguide according to claim 1, wherein:

the first conductor layer and the second conductor layer are each made of a negative permittivity medium having a negative dielectric constant real part for the electromagnetic wave in the waveguide mode;

the waveguide further comprises a core layer having a lamination structure including a semiconductor portion in contact with the first conductor layer and the second conductor layer and disposed between the first conductor layer and the second conductor layer;

the tapered structure is disposed at an end of the waveguide defined by the first conductor layer, the second conductor layer, and the core layer, at which the electromagnetic wave exits or enters; and the spatial profile of the tapered structure extends at least in a lamination direction of the core layer of the lamination structure to both sides with respect to a lamination surface perpendicular to the lamination direction as being closer to the opening plane at the outermost part of the tapered structure.

3. The waveguide according to claim 2, wherein:

the core layer has an electromagnetic wave gain; and the first conductor layer and the second conductor layer have a negative dielectric constant real part for the electromagnetic wave in the oscillation mode and are formed as an oscillation device.

4. The waveguide according to claim 2, wherein:

the tapered structure includes a first surface and a second surface which are inclined with respect to the lamination direction of the core layer; and the first surface and the second surface are disposed to be opposed to each other.

5. The waveguide according to claim 4, wherein:

the first conductor layer and the first surface are electrically connected to each other; and the second conductor layer and the second surface are electrically connected to each other.

6. The waveguide according to claim 4, further comprising:

a first substrate which is in contact with the first conductor layer and includes the first surface; and a second substrate which is in contact with the second conductor layer and includes the second surface, wherein the first substrate, the first conductor layer, the core layer, the second conductor layer, and the second substrate are laminated in this order.

7. The waveguide according to claim 2, wherein the core layer includes a multiple quantum well structure for generating a terahertz waves by intersubband transition of carriers.

8. The waveguide according to claim 1, wherein the tapered structure is electrically coupled to the waveguide.

9. The waveguide according to claim 1, wherein the tapered structure comprises a horn antenna formed by gradually extending an opening of a waveguide tube so as to be matched to free space.

10. The waveguide according to claim 2, wherein the first conductor layer and the second conductor layer have a negative dielectric constant real part for an electromagnetic wave to be detected and are formed as a detection device.

11. An electromagnetic wave analysis apparatus, comprising:

an oscillation device for oscillating an electromagnetic wave; and a detection device for detecting the electromagnetic wave after passing through an object or being reflected by the object, wherein at least one of the oscillation device and the detection device includes a waveguide, and wherein:

the waveguide is for guiding an electromagnetic wave between a first conductor layer and a second conductor layer of the waveguide each having a negative dielectric constant real part for the electromagnetic wave;

the first conductor layer and the second conductor layer are each made of a negative permittivity medium having a negative dielectric constant real part for the electromagnetic wave in a waveguide mode;

the waveguide comprises a tapered structure in a part of the waveguide at which the electromagnetic wave exits or enters;

a spatial profile of the tapered structure perpendicular to an optical axis extends to both sides with respect to the optical axis at least in one direction orthogonal to the optical axis as being closer to an opening plane at an outermost part of the tapered structure; and the first conductor layer and the second conductor layer are close to each other by a distance of a guide wavelength $\lambda_g = \lambda/n_e$ or smaller in one of a waveguide mode and an oscillation mode, where $\lambda$ represents a wavelength of the electromagnetic wave, and $n_e$ represents an equivalent refractive index of the waveguide.

* * * * *